United States Patent [19]
Allard et al.

[11] Patent Number: 5,509,937
[45] Date of Patent: Apr. 23, 1996

[54] PROSTHETIC FOOT WITH ENHANCED HEEL CONTROL

[75] Inventors: Paul Allard, Pierrefonds; Jean Dansereau, Ste-Thérèse; François Trudeau; Rony Herrera, both of Montréal, all of Canada

[73] Assignee: Université De Montréal, Montréal, Canada

[21] Appl. No.: 420,161

[22] Filed: Apr. 11, 1995

Related U.S. Application Data

[63] Continuation-in-part of Ser. No. 181,028, Jan. 14, 1994, Pat. No. 5,425,781.

[51] Int. Cl.$^6$ ........................ A61F 2/66
[52] U.S. Cl. ........................ 623/55; 623/54
[58] Field of Search .................. 623/55, 53, 47–52, 623/54, 56

[56] References Cited

U.S. PATENT DOCUMENTS

| | | | |
|---|---|---|---|
| 2,440,075 | 4/1948 | Campbell | 623/50 |
| 4,865,612 | 9/1989 | Arbogast et al. | 623/55 |
| 5,116,385 | 5/1992 | Allard et al. | 623/55 |
| 5,219,365 | 6/1993 | Sabolich | 623/55 |
| 5,258,039 | 11/1993 | Goh et al. | 623/55 |

FOREIGN PATENT DOCUMENTS

| | | | |
|---|---|---|---|
| 2698538 | 6/1994 | France | 623/55 |
| 9324080 | 12/1993 | WIPO | 623/53 |
| 9410942 | 5/1994 | WIPO | 623/53 |

*Primary Examiner*—David H. Willse
*Attorney, Agent, or Firm*—Francois Martineau; Pierre Lespérance

[57] ABSTRACT

A prosthetic foot keel comprising: (a) a generally S-shaped unitary spatula, defining a main forefoot leg, a rear leg, and an intermediate leg integrally joining the forefoot and rear legs; and (b) a generally C-shape heel, defining a top heel plate, a bottom heel plate, and an intermediate heel plate transversely integrally interconnecting the top and bottom heel plates; wherein said top heel plate is fixedly anchored against the underface of the spatula rear leg. A generally open pocket is defined by the heel and by the spatula intermediate and rear legs. The pocket opens both rearwardly of the foot keel and laterally outwardly thereof on the side opposite the intermediate heel part. The shape of the open pocket is resiliently deformable responsively to the cyclical loads sustained by the spatula forefoot leg and bottom heel plate during the wearer's gait.

13 Claims, 5 Drawing Sheets

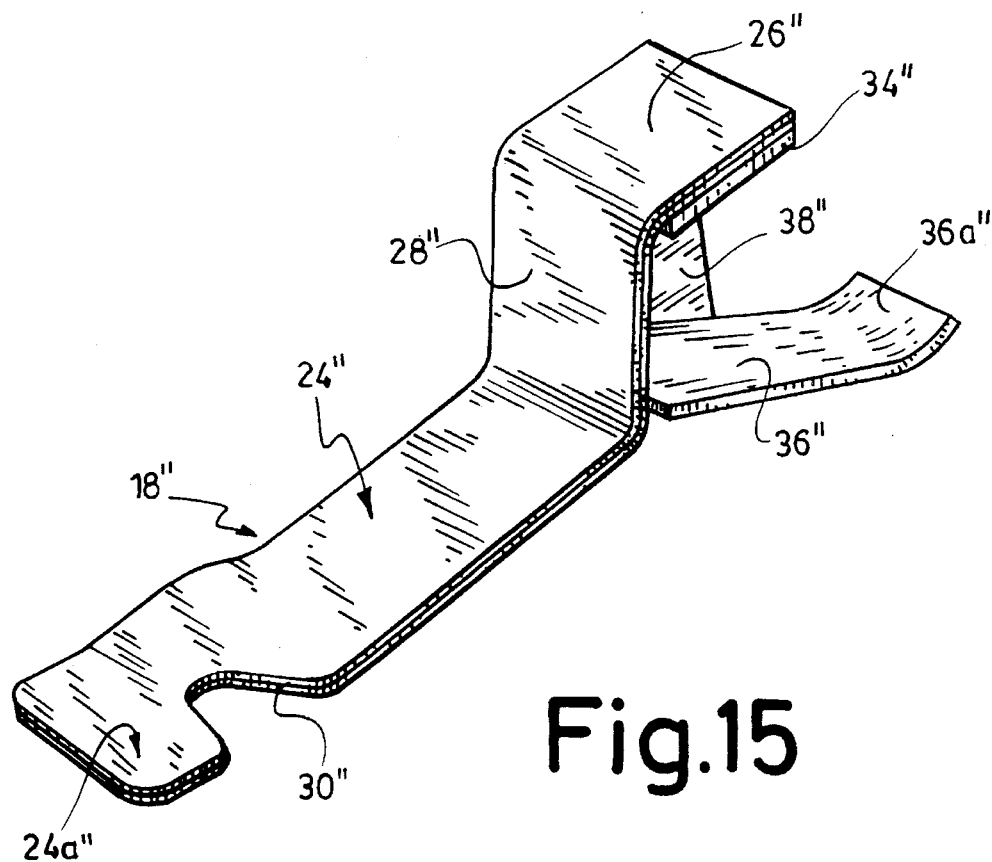
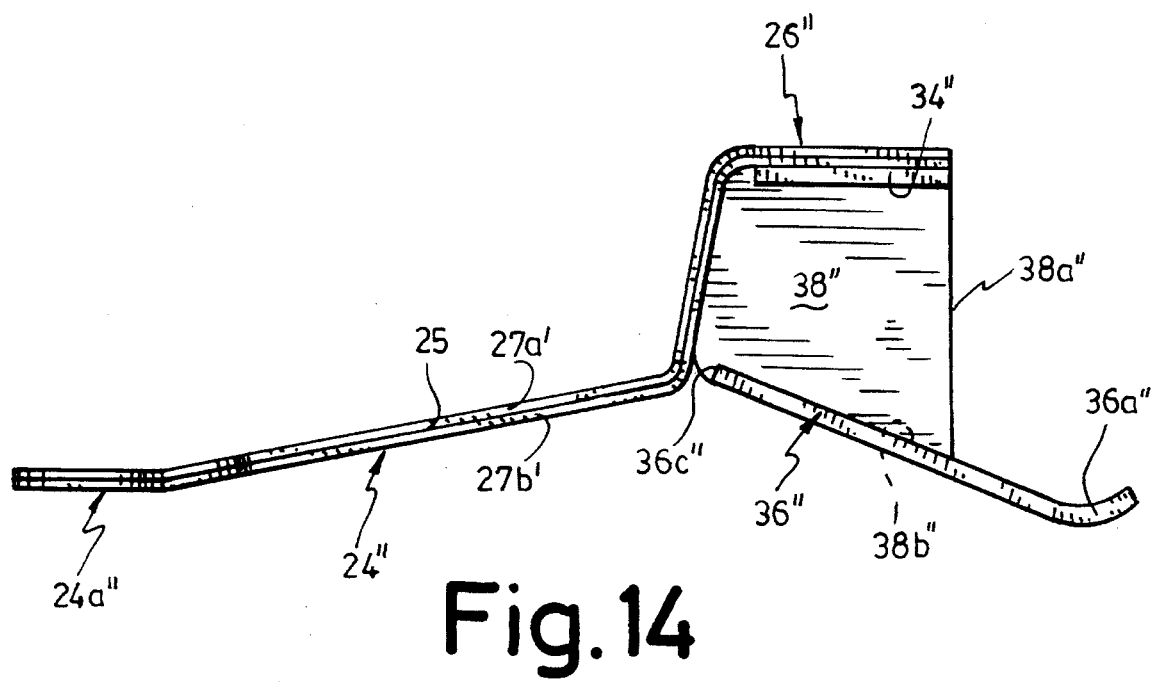

PROSTHETIC FOOT WITH ENHANCED HEEL CONTROL

CROSS-REFERENCE DATA

This application is a Continuation-In-Part of U.S. patent application Ser. No. 08\181,028, filed Jan. 14, 1994, now U.S. Pat. No. 5,425,781.

FIELD OF THE INVENTION

This invention relates to artificial leg part devices that are to fit the stump of amputated persons, for enabling same to at least partially resume life-like leg movement.

BACKGROUND OF THE INVENTION

In said co-pending patent application Ser. No. 08\181, 028, there is disclosed a prosthetic foot to be fixedly secured by an attachment means to a prosthetic leg. This prosthetic foot consists of a cantilever spring monolithic member made from a substantially rigid, yet resiliently elastic material, and forming an elongated band defining one and another lateral side edges. The band is formed of two coextensive integral parts including an elongated forefoot part and a C-shape aft heel part. The C-shape of said heel part is medio-laterally oriented and defines a straight, free, outer end portion, an opposite, straight, inner end portion substantially parallel to said outer end portion, and an arcuate portion integrally joining a fore fraction of said heel part inner and outer end portions, whereby the thus formed aft fraction of said heel part inner and outer end portions not joined by said arcuate portion define a sagittal gap spacing therebetween such that said aft fraction of the heel part outer end portion spacedly overlies the aft fraction of said heel part inner end portion. The gap spacing is of variable magnitude upon a load being applied against the aft end of said elastic heel part outer end to resiliently bias same toward the aft end of said heel part inner end. The heel part outer end portion further has attachment means, for connection to an upper prosthesis.

In this co-pending application, a flange projects transversely from said another lateral side edge of said forefoot part integrally thereto. The band also includes a curved part, integrally interconnecting said forefoot part and said heel part inner end portion. The curved part is curved toward a plane intersecting said heel part free end portion, whereby said heel part, forefoot part and curved part extend substantially within a single selected plane. The forefoot flange projects outwardly from and about an axis orthogonal to said sagittal plane.

Hence, upon said cantilever spring member of this copending patent application being fitted to an amputee's limb through said attachment means, said cantilever spring member, during gait, will absorb energy at said heel part during prosthetic foot heel strike, will store said energy, to provide medio-lateral control at heel-strike, will restore said energy at foot push-off in such a way as to provide substantial medio-lateral control of the prosthetic foot during both loading and unloading of the prosthetic foot keel, as well as shock dampening capability at heel strike.

OBJECT OF THE INVENTION

The gist of the invention is to improve upon the prosthetic foot disclosed in co-pending patent application Ser. No. 8\181,028, whereby the top leg of the C-shape heel part is directly connected to the forefoot part of the prosthetic foot.

SUMMARY OF THE INVENTION

Accordingly the object of the invention, there is disclosed a resilient prosthetic foot keel comprising: (a) a unitary, preferably S-shape, spatula member, defining an elongated, lower, fore and aft extending forefoot member, an upper fore and aft extending rear member, and a generally wavy intermediate member integrally transversely joining said forefoot and rear members in an axially offset fashion; (b) a generally arcuate, preferably C-shape, unitary heel member, defining a flat top heel part, a bottom heel part, and an intermediate heel part transversely integrally interconnecting said top and bottom heel parts; and (c) attachment means, fixedly interconnecting said top heel part to said spatula rear member; wherein a generally open pocket is defined by said heel member and by said spatula intermediate and rear members, said pocket opening both rearwardly of the foot keel and laterally outwardly thereof on the side opposite said intermediate heel part, and wherein the shape of said open pocket is resiliently deformable responsively to the cyclical loads sustained by the spatula forefoot member and bottom heel part during the wearer's gait. Preferably, a notch is made laterally of the front free end portion defined by said spatula forefoot member, wherein said notch is located on the side opposite that of said intermediate heel part.

In one embodiment of the invention, the bottom heel part could be made substantially coplanar to said spatula forefoot member. The bottom heel part could then include a rearward extension section, extending well beyond the rear ends defined by said top and intermediate heel parts. In this embodiment, a foot-size plastic coating must cover and embed the prosthetic foot keel for the keel to be operational.

Another feature of the invention could be that said front portion of the spatula forefoot member be laterally elbowed, so as to be slightly offset axially from the remaining portion of said spatula forefoot member, said lateral offset occurring on the side opposite that of said notch.

According to an alternate embodiment of the invention, said intermediate heel part is longer than said spatula intermediate member, wherein said bottom heel part is downwardly offset relative to the plane of said spatula forefoot member. It could then be envisioned that said bottom heel part and said spatula forefoot member be downwardly forwardly inclined relative to intersecting planes that are parallel to said top heel part. The front free end portion of said spatula forefoot member could then be slightly upwardly elbowed relative to the remaining portion of said spatula forefoot member.

In another embodiment of the invention, said bottom heel part could be downwardly rearwardly inclined, and said spatula forefoot member could be downwardly forwardly inclined. The rear free end portion of said downwardly rearwardly inclined bottom heel part could then form an upwardly arcuate flange.

In both the second and third embodiments of the invention, providing a foot-size plastic coating for covering and\or embedding the prosthetic foot keel is optional (e.g. for aesthetic purposes).

BRIEF DESCRIPTION OF THE DRAWINGS

FIG. 14 is a side elevational view of a right-hand side prosthetic foot being provided accordingly with the invention with a third embodiment of heel element; and FIG. 15 is an isometric view of the prosthetic foot of FIG. 14.

DETAILED DESCRIPTION OF THE DRAWINGS

Figure 1:
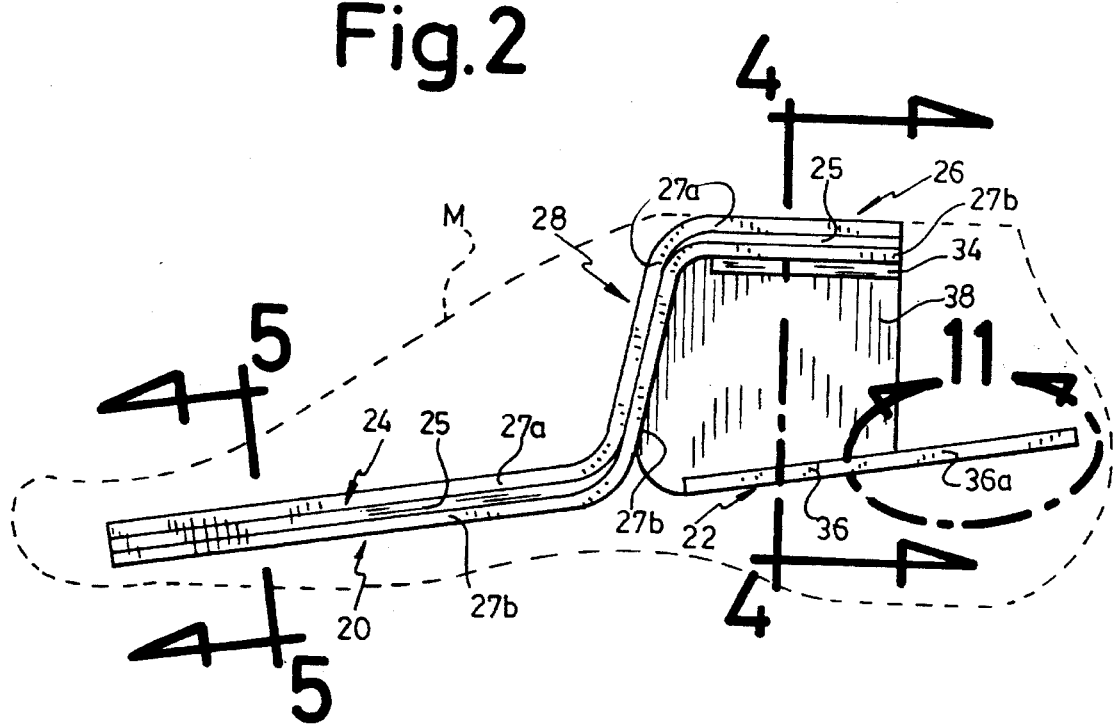
FIG. 1 is a side elevational view of a right-hand side prosthetic foot according to a preferred embodiment of the invention, showing in dotted lines the contour of a soft, foot-like body.
Figure 3:
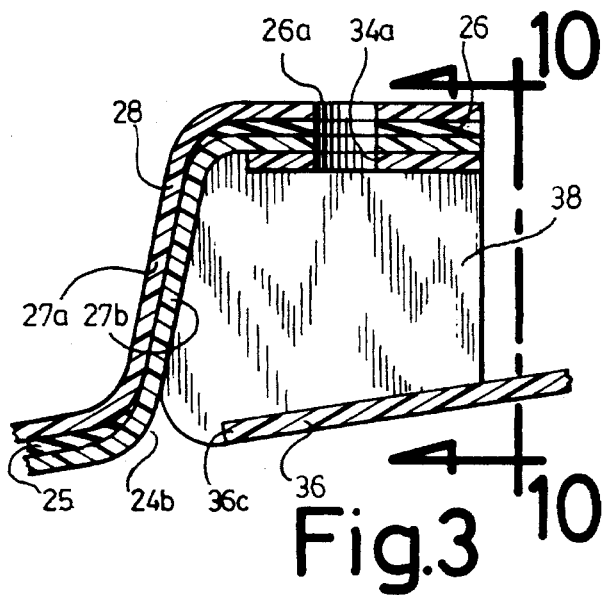
FIG. 3 is a sectional view taken along line 3—3 of FIG. 2.
Figure 5:
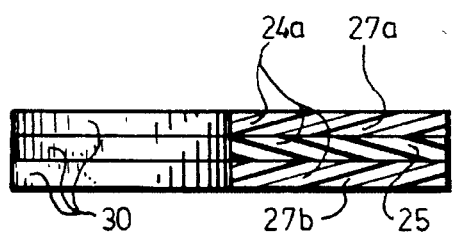
FIG. 5 is an enlarged cross-sectional view taken along line 5—5 of FIG. 1.
Figure 4:
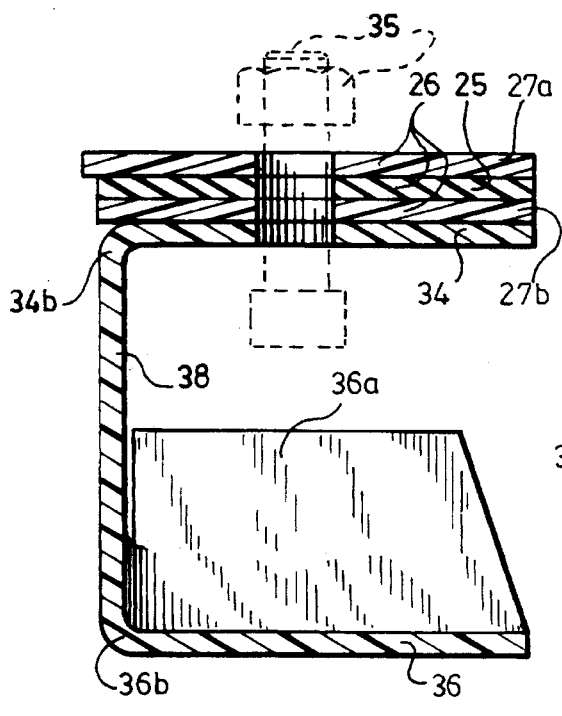
FIG. 4 is an enlarged cross-sectional view taken along line 4—4 of FIG. 1.

As illustrated in FIGS. 1 to 11 of the drawings, the prosthetic foot keel 18 according to a first embodiment of the invention includes two main elements: a forefoot element 20, and a heel element 22. Forefoot element 20 forms a generally rectangular blade in top plan view (see FIG. 2), and an S-shape spatula in side edge view (FIG. 1). The forefoot element blade more particularly includes a straight front leg 24, a rear flat leg 26, and an intermediate transverse leg 28 integrally joining the front and rear legs 24 and 26, so that an "S shape" be formed in edgewise view. Front leg 24 includes a front end portion 24a, which is offset from the main body of the front leg 24, and which includes a rounded lateral notch 30 on its lateral side opposite that of said offset thereof. Rear leg 26 includes a bore 26a, for transverse engagement by the stud member 35 (FIG. 4) of an attachment means (not shown) for interconnecting the prosthetic foot 18 to a wearer's leg.

Spatula 20 is made of a resiliently flexible, relatively hard material, so that, during keel propulsion, the spatula can be temporarily deformed yieldingly to a load applied cyclically during gait of the wearer. Keel deformation occurs about the intermediate transverse leg 28 of the spatula 20, whereby the relative angle between the planes intersecting the forefoot leg 24 and the rear leg 26 of the spatula will vary.

Preferably, and as suggested in the drawings, the forefoot leg 24 and the top rear leg 26 of the spatula 20 will both accordingly be made of a main intermediate sheet layer of elastomeric material 25, being taken in sandwich between a pair of top and bottom sheet layers of carbon fibres 27a, 27b. A suitable glue compound, e.g. a resin solution into which is embedded these three layers 25, 27a, 27b, fixedly interconnects these three layers. This main intermediate elastomeric sheet layer 25 absorbs or dampens the blows or loads sustained when the prosthetic foot keel 18 strikes and engages ground B. This main intermediate sheet layer of elastomeric material tapers off about the two opposite elbowed ends of the spatula intermediate leg 28, so as to fully disappear in leg 28. Hence, spatula intermediate leg 28 would consist only of a bilayer of carbon fibres 27a, 27b, being fixedly interconnected by a suitable glue compound, e.g. being embedded in a resin solution. The main elastomeric sheet layer 25 has been removed about the spatula intermediate section 28, so as to provide a more sturdy fixed interconnection between the two carbon fiber layers 27a, 27b, relative to the interconnection achieved between the three layers 25, 27a, 27b, of each spatula section 24 and 28.

Preferably, the front and rear ends of each sheet layer of elastomeric material come in transverse register (are "flush") with that of the intermediate layer of carbon fibres, as illustrated in the drawings, although this is not critical.

Figure 2:
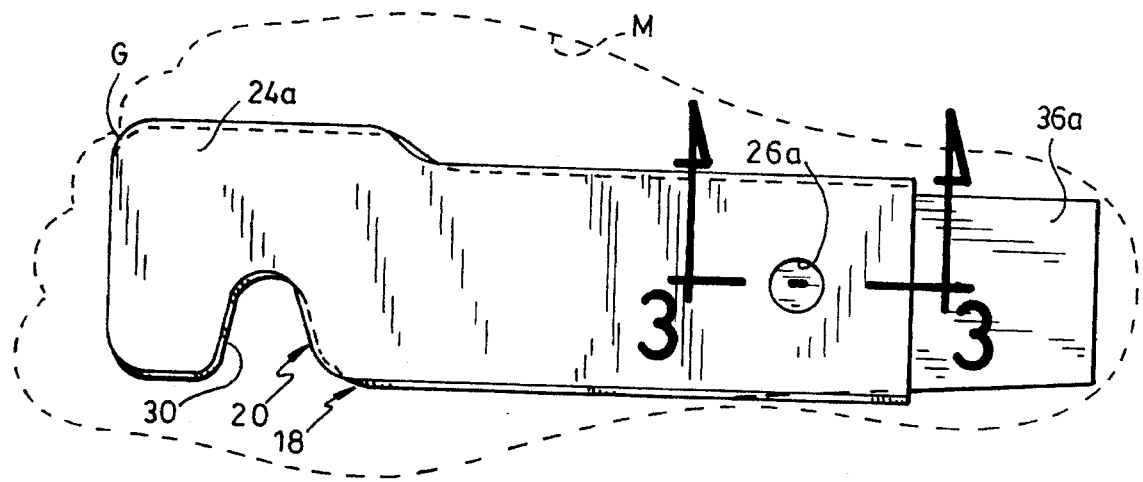
FIG. 2 is a top plan view of the prosthetic foot of FIG. 1.
Figure 6:
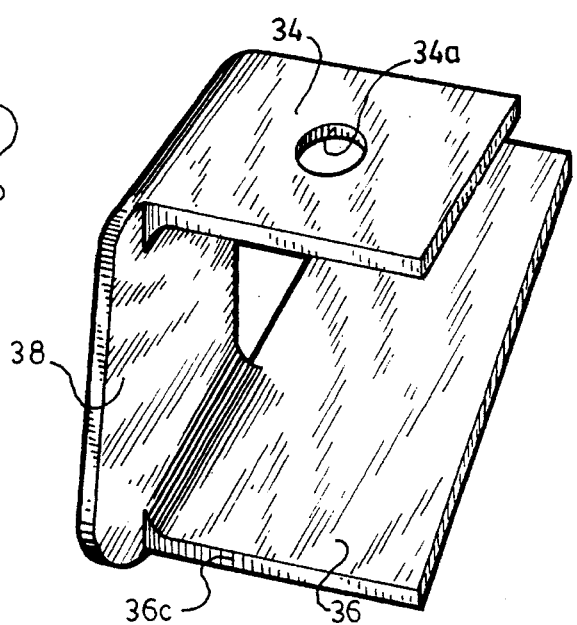
FIG. 6 is an isometric view of a heel element, according to a first embodiment of the invention, and forming part of the prosthetic foot of FIG. 1.

The heel element 22 includes a top plate 34, a bottom plate 36, and an intermediate plate 38 transversely interconnecting the top and bottom plates 34 and 36. In this particular embodiment of the invention, all three plates 34, 36, 38, are of generally square shape. Top plate 34 includes a bore 34a coming in register with the spatula bore 26a, and is sized to fit generally beneath and in register with the rear leg 26 of the spatula 20 and is integrally connected therewith. Coaxial bores 26a and 34a are adapted to be axially engaged by the stub 35 (FIG. 4) of a lump attachment member, not shown, for fixedly interconnecting the keel 18 to an artificial leg. Preferably, bores 26a, 34a, will be cylindrical, as illustrated in FIGS. 2 and 6, for axial engagement by a correspondingly cylindrical stub 35 from the lump attachment member.

In this first embodiment, bottom plate 36 extends generally coaxially to the spatula front leg 24, and its rear edge portion 36a projects rearwardly beyond the transversely registering rear edge of top plate 34 and rear edge 26b of the spatula rear leg 26. The front edge 36c (FIG. 3) of the bottom plate 36 extends spacedly short of the rear end 24b of the spatula front leg 24, as clearly shown in FIG. 3. Intermediate plate 38 edgewisely fixedly interconnects the lateral side edges 34b, 36b, (FIG. 4) of plates 34 and 36 (exclusively of rearwardly projecting rear edge portion 36a), but exclusively of the lateral side edge 28b (FIG. 10) of the spatula intermediate leg 28, wherein edges 34b, 36b and 28b are located on the side of the prosthetic foot keel 18 opposite the spatula front notch 30. Intermediate plate 38 should be generally flat, or have a somewhat arcuate shallow shape, as suggested in FIG. 6 of the drawings.

Preferably, the three legs 34, 36, 38, of the heel member 22 are all made from a single layer of carbon fibres embedded into a resin solution.

Figure 7:
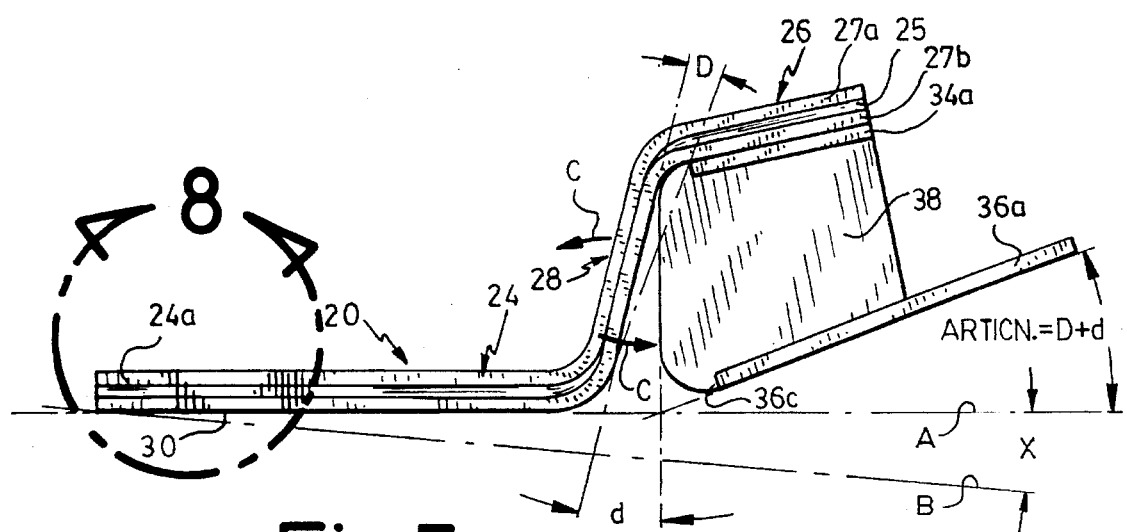
FIG. 7 is a side elevational view of the prosthetic foot of FIG. 1, suggesting the available relative movement play of the heel element relative to the spatula element of the prosthetic foot.
Figures 8, 9:
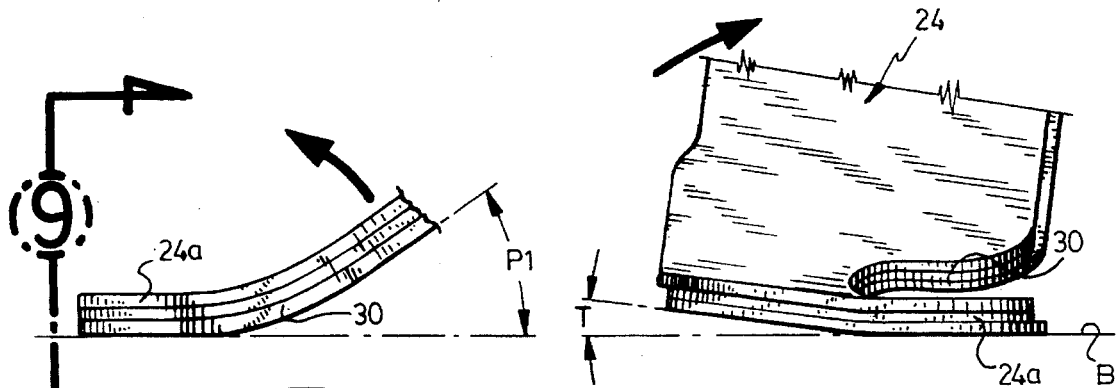
FIG. 8 is an enlarged view of the area circumscribed by circle 8 in FIG. 7, but showing the spatula being partially flexed upwardly as suggested by the bold arrow.
FIG. 9 is a front end elevational view of the spatula, taken from perspective 9—9 of FIG. 8.

FIGS. 7 and 8 suggest how the lateral C-shape heel part 22 can tilt rearwardly and upwardly, spacedly away from the intermediate leg 28 of the spatula 20, responsively to a toe-in ground propulsion load being applied at an angle about the front portion 24a of the spatula forefoot leg 24. For example, with a 10° relative angle between the plane A of the spatula forefoot leg 24 and the ground level B, a limited rearwardly downwardly inclined tilting motion of the spatula intermediate leg 28 will occur, as suggested by arrow C in FIG. 7, to reach a spatula condition as illustrated in FIG. 7, when the spatula front portion 24a pushes against the ground B.

FIG. 9 suggests how medio-lateral control of the prosthetic foot keel 18 during foot propulsion is achieved, when the interior lateral side edge (on the side of notch 30) of the spatula forefoot leg front portion 24a engages ground B before the opposite exterior lateral side edge thereof. Torsional forces therefore result, being enhanced by the notch 30 formed laterally of the spatula front portion 24a, and as generally disclosed in prior U.S. Pat. No. 5,116,385 issued in 1992 to some of the present joint inventors.

Figures 10, 11:
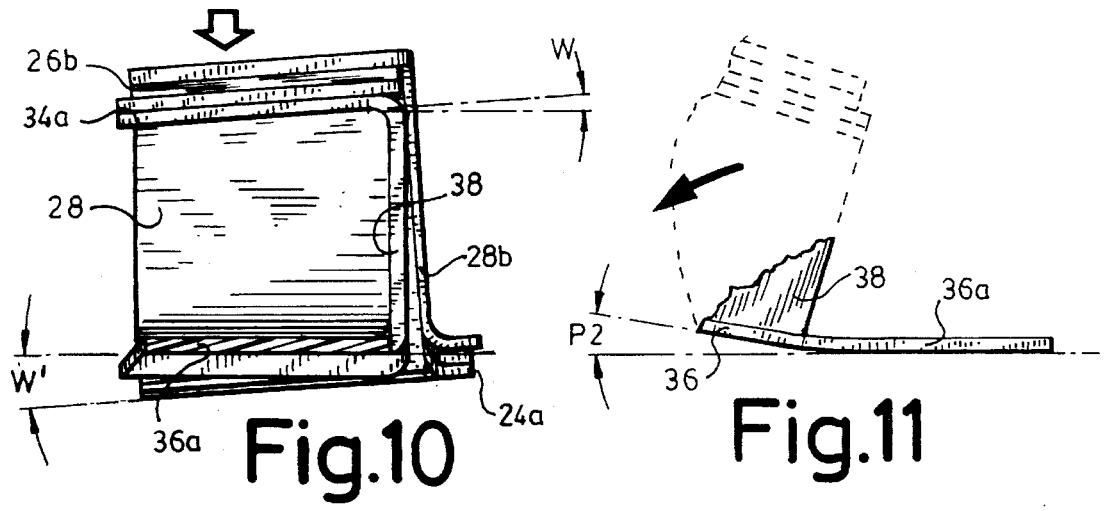
FIG. 10 is a rear end elevational view of the heel element, taken from perspective 10—10 of FIG. 3.
FIG. 11 is an enlarged view of the area circumscribed by ellipse 11 in FIG. 1, but showing the bottom leg of the heel element being partially flexed abuttingly against the ground, and the whole keel moving downwardly to the ground as suggested by the bold arrow.

FIGS. 10 and 11 suggest in turn how the C-shape heel member 34, 36, 38, is deformed under torsional forces, during heel strike. FIG. 10 shows more specifically how the heel 34–38 absorbs and stores the medio lateral loads during heel strike, by interiorly deforming about bottom plate 36 as indicated by angular value w'. FIG. 11 shows the heel deformation during heel strike, in the sagittal plane: the arrow suggests that the whole prosthetic foot keel 18 is moving downwardly to the ground B, pivotingly about ground abutment rear leg 36a.

During gait, there is cyclical foot reception to the ground. The heel part 34–38 of the prosthetic foot keel 18 is most often the first to strike ground B, during foot reception. At this moment, the rearmost part 36a of the heel (FIG. 11) becomes deformed in the sagittal plane as well as in the frontal plane (FIG. 10), thus dampening weight load transfer from the natural leg to the amputated leg. This load imposed to the keel 18 at this step of gait will bias the rear part 34–38 of the keel, to deform by partly closing the square C formed by the plates 34, 38, 36, thus providing medio lateral control at ground reception (heel strike).

Thereafter, foot keel rotation will continue until the foot spatula 20 is flat over ground B. The rear part 34–38 of the foot keel 18 facilitates this rotation by resuming its initial shape, through deformation energy restoration which had built up during heel strike. When the rear part 34–38 of the foot keel 18 has resumed its original unbiased shape, it is then the front part 24a of the spatula 20 which is now in ground-engaging contact, to push the keel 18 off the ground B.

Rotation still continues and the keel 18 deforms as illustrated in FIG. 7; the heel raises and angular value D increases. The keel 18 stores energy from deformation, while the wearer prepares to shift his weight from the amputated leg to his natural leg. At this point in time, all the wearer's weight is supported to the front 24 of the keel 18, wherein the keel front part 24a becomes deformed as illustrated in FIGS. 8 and 9. Such a deformation thus occurs by flexion (FIG. 8) and by torsion (FIG. 9) of spatula front leg 24. When weight transfer is completed, the thus deformed spatula 20 regains its original shape, restoring stored energy and propulsing the amputated leg forwardly and interiorly, thus promoting weight load transfer.

Figure 12:
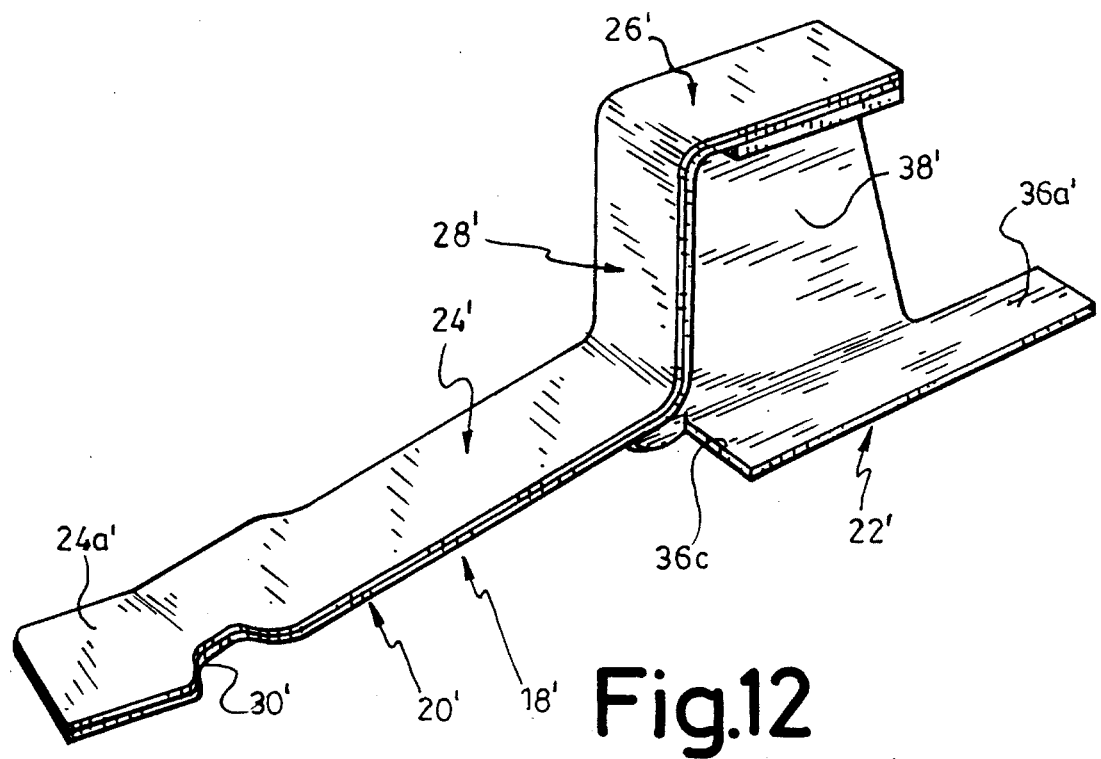
FIG. 12 is an isometric view of a right-hand side prosthetic foot being provided accordingly with the invention with a second embodiment of heel element.
Figure 13:
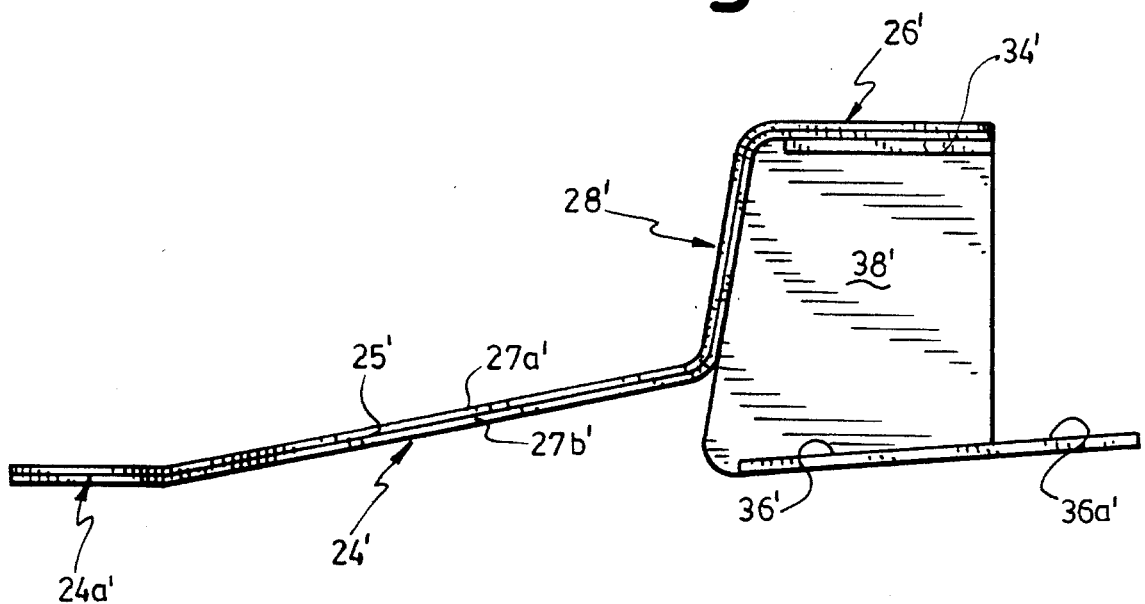
FIG. 13 is a side elevational view of the prosthetic foot of FIG. 12.

In the alternate embodiment of the invention illustrated in FIGS. 12–13 of the drawings, there is shown a prosthetic foot keel that is similar in most respect to the first embodiment, whereby all corresponding reference numerals are single primed. The three main differences are as follows:

1. the intermediate heel plate 38' is longer in height, i.e. is rectangular rather than square, whereby the bottom edge thereof extends beyond the plane intersecting the spatula forefoot leg 24'. That is to say, the bottom plate 36' is downwardly offset relative to forefoot leg 24'.

2. the heel bottom plate 36' has been downwardly forwardly tilted, so that it is no longer coplanar nor parallel to forefoot leg 24', but rather, extends within a plane generally parallel to heel top plate 34' while converging somewhat toward a virtual axial extension of forefoot leg 24'.

3. the front portion 24a' of the spatula forefoot leg 24' becomes slightly upwardly tilted relative to the plane of the main section 24' of the spatula forefoot leg, whereby a small elbow is formed therebetween.

In the third embodiment of the invention illustrated in FIGS. 14–15 of the drawings, there is shown a prosthetic foot keel that is similar in most respect to the second embodiment, whereby all corresponding reference numerals are double primed. The three main differences are as follows:

1. the heel intermediate plate 38" is trapezoidal, with its rear edge 38a" being longest, whereby its bottom edge 38b" is downwardly rearwardly inclined.

2. The heel bottom plate 36" is downwardly rearwardly inclined.

3. The rear end portion 36a" of the heel bottom plate 36" forms an upturned arcuate flange.

It is understood that, as suggested in FIGS. 1 and 2 of the drawings, any one of the three above-described embodiments of cantilever spring type prosthetic foot keels 18, 18', 18", can be covered by a variable thickness coating of skin-like coating material M. Material M will preferably consist of a soft elastomeric material, or a relatively rigid polymeric material, which is cured thereon; whereby the resulting artificial foot member is sized to conform to the shape and size of a life-like foot. However, the first embodiment of keel, 18, must be coated with and embedded in the skin-like material M (as suggested in FIG. 1), to be functional, i.e. the keel 18 must be completely bedded in the elastomeric or polymeric material M, so that the foot-like mass of material M be full. The reason why the foot-like mass of material M cannot simply be a hollow sheathing surrounding the keel (e.g., for aesthetic purposes) is that the heel part 34–38 of the keel 18 is far too distant from the heel part of the foot-like stump member to be operative. On the other hand, either one of the second and third embodiments 18', 18" of keels will still be functional, even if only a hollow foot-like sheath of material M is formed around the keel (simply for aesthetic purposes to improve the looks thereof), i.e. without the keels 18' or 18" needing to be bedded in a full mass of the skin-like material M.

FIG. 2 shows that the spatula front portion 24a in general, and the laterally exterior side edge thereof in particular, extends very close to the "toe"-like part of the foot-like mass of material M. However, it is envisioned that this gap G between the toes and the spatula portion 24a be substantially increased, accordingly with the specific requirements of the wearer. Therefore, the edgewise contour of the coating material M around the keel 18, as illustrated in FIGS. 1 and 2, can be modified in a variety of suitable ways, within the scope of the invention.

I claim:

The embodiments of the invention for which an exclusive property or privilege is claimed, are defined as follows:

1. A resilient prosthetic foot keel comprising:

(a) a unitary spatula member, defining an elongated, lower, fore and aft extending forefoot member, an upper fore and aft extending rear member, and a generally wavy intermediate member integrally transversely joining said forefoot and rear members in an axially offset fashion;

(b) a generally arcuate unitary heel member, defining a flat top heel part, a bottom heel part, and an intermediate heel part transversely integrally interconnecting said top and bottom heel parts; and (c) attachment means, fixedly interconnecting said top heel part to said spatula rear member;

wherein a generally open pocket is defined by said heel member and by said spatula intermediate and rear members, said pocket opening both rearwardly of the foot keel and laterally outwardly thereof on the side opposite said intermediate heel part, and wherein the shape of said open pocket is resiliently deformable responsively to the cyclical loads sustained by the spatula forefoot member and bottom heel part during the wearer's gait.

2. A prosthetic foot keel as defined in claim 1, further including a notch, made laterally of the front free end portion defined by said spatula forefoot member, wherein said notch is located on the side opposite that of said intermediate heel part.

3. A prosthetic foot keel as defined in claim 2, wherein said bottom heel part is substantially coplanar to said spatula forefoot member.

4. A prosthetic foot keel as defined in claim 3, wherein said bottom heel part includes a rearward extension section, extending well beyond the rear ends defined by said top and intermediate heel parts.

5. A prosthetic foot keel as defined in claim 2, wherein said front portion of the spatula forefoot member is laterally elbowed so as to be slightly offset axially from the remaining portion of said spatula forefoot member, said lateral offset occurring on the side opposite that of said notch.

6. A prosthetic foot keel as defined in claim 1, wherein said intermediate heel part is longer than said spatula intermediate member, wherein said bottom heel part is downwardly offset relative to the plane of said spatula forefoot member.

7. A prosthetic foot keel as defined in claim 6, wherein said bottom heel part and said spatula forefoot member are downwardly forwardly inclined relative to intersecting planes that are parallel to said top heel part.

8. A prosthetic foot keel as defined in claim 7, further including a notch, made laterally of the front free end portion of said spatula forefoot member, wherein said notch is located on the side opposite that of said intermediate heel part; wherein the front free end portion of said spatula forefoot member is slightly upwardly elbowed relative to the remaining portion of said spatula forefoot member.

9. A prosthetic foot keel as defined in claim 1, wherein said bottom heel part is downwardly rearwardly inclined, and said spatula forefoot member is downwardly forwardly inclined.

10. A prosthetic foot keel as defined in claim 9, wherein the rear free end portion of said downwardly rearwardly inclined bottom heel part forms an upwardly arcuate flange.

11. A prosthetic foot keel as defined in claim 1, wherein said spatula is generally S-shaped.

12. A prosthetic foot keel as defined in claim 1, wherein said heel member is generally C-shape.

13. A prosthetic foot keel as defined in claim 1, wherein said forefoot member and said rear member of said spatula member are both made of a main intermediate sheet layer of elastomeric material, being taken in sandwich between a pair of sheet layers of carbon fibres embedded in a resin solution, while said main intermediate sheet layer of elastomeric material tapers off about the two opposite elbowed ends of said spatula intermediate member, so as to fully disappear in said spatula intermediate member which consists only of a bilayer of carbon fibres embedded in a resin solution; and said heel member is made from a single layer of carbon fibres embedded into a resin solution.

* * * * *